(12) United States Patent
Mileham et al.

(10) Patent No.: US 6,410,227 B1
(45) Date of Patent: *Jun. 25, 2002

(54) DNA MARKERS FOR LITTER SIZE

(75) Inventors: John Alan Mileham, Comberton; Graham Stuart Plastow, Shipdham; Olwen Irene Southwood, Wantage, all of (GB)

(73) Assignee: Dalgety PLC, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,915

(22) Filed: Dec. 12, 1997

Related U.S. Application Data

(63) Continuation of application No. PCT/GB96/01408, filed on Jun. 12, 1996.

(30) Foreign Application Priority Data

Jun. 12, 1995 (GB) .............................................. 9511888

(51) Int. Cl.$^7$ ........................... C12Q 1/68; C12P 19/34; C07H 21/02
(52) U.S. Cl. ......................... 435/6; 435/91.1; 435/91.2; 435/91.21; 536/23.1; 536/24.3; 536/24.31; 536/24.32; 536/24.33
(58) Field of Search ......................... 435/6, 91.1, 91.2, 435/91.21; 536/23.1, 24.3, 24.31, 24.32, 24.33

(56) References Cited

U.S. PATENT DOCUMENTS 5,550,024 A * 8/1996 Rothschild et al. ............ 435/6

FOREIGN PATENT DOCUMENTS

| WO | WO9218651 | 10/1992 |
|---|---|---|
| WO | WO9641892 | 12/1996 |

OTHER PUBLICATIONS

Montgomery, G.W. et al., "Physiology and Molecular Genetics of Mutations that Increase Ovulation Rate in Sheep", *Endocrine Reviews*, vol. 13, No. 2, pp.

Ellegren, Hans, et al., "Conserved Synteny between Pig Chromosome 8 and Human Chromosome 4 but Rearranged and Distorted Linkage Maps", *Genomics*, vol. 17 (1993) pp. 599–603

Montgomery, G.W., et al., "The Search for the Booroola (FecB) Mutation", *Journal of Reproduction and Fertility Supplement*, vol. 49 (1995) pp. 113–121.

Montgomery et al, "The ovine booroola fecundity gene (fecB) is linked to markers from a region of human chromosome 4q", Nature Genetics 4(4):410–414, Aug. 1993.*

Zhang et al., "Characterization of the promoter region of the porcine opn (osteopontin, screted phosphoprotein 1) gene", Eur. J. Biochem. 207:649–659, 1992.*

Andersson et al., "Genetic Mapping of Quantitative Trait Loci for Growth and Fatness in Pigs", *Science*, 25 Mar. 1994, 263:1771–1774.

Bernstein et al., "The mouse W/c–kit locus", *Molecular Control of Haemopoiesis*, 1990, Ciba Foundation Symposium 148:158–172.

Besmer et al., "A new acute transforming feline retrovirus and relationship of its oncogene v–kit with the protein kinase gene family", Apr. 3, 1986, *Nature* 320:415–421.

Chabot et al., "The proto–oncogene c–kit encoding a transmembrane tyrosine kinase receptor maps to the mouse W locus", Sep. 1, 1988, *Letters to Nature* 335:88–89.

Coppieters et al., "Characterization of porcine microsatellite loci", 1993, *Animal Genetics* 24:163–170.

De Sepulveda et al., "Instability at the W/c–kit locus in mice: analysis of melanocyte cell lines derived from reversion spots", 1994, *Oncogene* 9:2655–2661.

Ezashi et al., "The gene for the βsubunit of porcine LH: clusters of GC boxes and CACCC elements", 1990, *Journal of Molecular Endocrinology* 5:137–146.

Fleischman et al., "Deletion of the c–kit protooncogene in the human developmental defect piebald trait", Dec. 1991, *Proc. Natl. Acad. Sci., USA* 88:10885–10889.

Giebel et al., "Organization and nucleotide sequence of the human KIT (mast/stem cell growth factor receptor) proto–oncogene", 1992, *Oncongene* 7:2207–2217.

Geissler et al., "The Dominant–White Spotting (W) Locus of the Mouse Encodes the c–kit Proto–Oncogene", Oct. 7, 1988, *Cell* 55:185–192.

Gokkel et al., "Structural organization of the murine c–kit proto–oncogene", 1992, *Oncogene* 7:1423–1429.

Johansson et al., "The Gene of Dominant White color in the Pig Is Closely Linked to ALB and PDGFRA on Chromosome 8", 1992, *Genomics* 14:965–969.

Kato et al., "The gene for the common αsubunit of porcine pituitary glycoprotein hormone", 1991, *Journal of Molecular Endocrinology* 7:27–34.

Nocka et al., "Molecular bases of dominant negative and loss of function mutations at the murine c–kit/white spotting locus: $W^{37}$, $W^v$, $W^{41}$, and W", 1990, *The EMBO Journal* vol. 9 No. 6:1805–1813.

Rohrer et al., "A Microsatellite Linkage Map of the Porcine Genome", Jan. 1994, *Genetics* 136:231–245.

* cited by examiner

*Primary Examiner*—Jeffrey Fredman
(74) *Attorney, Agent, or Firm*—Brobeck, Phleger & Harrison, LLP

(57) ABSTRACT

Methods for screening pigs to determine which are more likely to produce larger litters and/or are less likely to produce larger litters are provided, based on identification of OPN alleles present in a sample of pig genomic DNA. Kits for use in such methods are also provided.

21 Claims, No Drawings

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: primer that can hybrid ise to flanking regions
      of pig microsatellites sequences
<220> FEATURE:
<221> NAME/KEY: satellite
<222> LOCATION: (1)..(24)

<400> SEQUENCE: 1
gctagttaat gacattgtac ataa                                          24

<210> SEQ ID NO 2
<211> LENGTH: 22
<212> TYPE: DNA
<213> ORGANISM: Artificial Sequence
<220> FEATURE:

```
-continued

<223> OTHER INFORMATION: Primer that can hybrid ise to flanking regions
      of pig microsatellites sequences
<220> FEATURE:
<221> NAME/KEY: satellite
<222> LOCATION: (1)..(22)

<400> SEQUENCE: 2
ccaatcctat tcacgaaaaa gc                                              22

<210> SEQ ID NO 3
<211> LENGTH: 24
<212> TYPE: DNA
<213> ORGANISM: Artificial Sequence
<220> FEATURE:
<223> OTHER INFORMATION: primer that can hybrid ise to flanking regions
      of pig microsatellite sequences
<220> FEATURE:
<221> NAME/KEY: satellite
<222> LOCATION: (1)..(24)

<400> SEQUENCE: 3
gtgtcatgag gtttttttcca ctgc                                           24

<210> SEQ ID NO 4
<211> LENGTH: 18
<212> TYPE: DNA
<213> ORGANISM: Artificial Sequence
<220> FEATURE:
<223> OTHER INFORMATION: primer that can hybrid ise to flanking regions
      of pig microsatellites sequences
<220> FEATURE:
<221> NAME/KEY: satellite
<222> LOCATION: (1)..(18)

<400> SEQUENCE: 4
caacccactt gctcccac                                                   18

<210> SEQ ID NO 5
<211> LENGTH: 24
<212> TYPE: DNA
<213> ORGANISM: Artificial Sequence
<220> FEATURE:
<223> OTHER INFORMATION: primer that can hybrid ise to flanking regions
      of pig microsatellites sequences
<220> FEATURE:
<221> NAME/KEY: satellite
<222> LOCATION: (1)..(24)

<400> SEQUENCE: 5
gtgtcatgag gtttgtgcca ctgc                                            24
```

DNA MARKERS FOR LITTER SIZE

This application is a continuation of PCT/GB96/01408 filed Jun. 12, 1996.

The present invention relates to methods of screening pigs to determine the presence or absence of osteopontin (OPN) alleles associated with increased litter size, to the use of such methods in predicting litter size in pigs and to kits for carrying out such methods.

Meat production and animal breeding efficiencies could be improved if it were possible to increase animal litter sizes. The same output of livestock could be derived from fewer parent animals, thus providing decreased production costs. In addition, animal breeding organisations would benefit from the potential to screen more offspring for those with improved genetics. However, litter size is very difficult to select for conventionally as it is limited to one sex and is heavily influenced by non-genetic factors (heritability, a measure of the fraction of the phenotypic variation that is due to genetic differences is approximately 0.1 for litter size in the pig).

One approach to improving litter size might be to introduce beneficial genes into production lines from breeds which have significantly higher litter sizes. However, quantitative genetics suggests that complex traits such as litter size are controlled by a large number of genes each having a small effect on the trait. If this is true, genetic progress through selection of complex traits is likely to be very slow. An alternative view is that, although many genes are involved in complex traits, a few of the genes involved (major genes) have large effects on the trait. If this alternative view is true, then genetic progress of such traits could be rapid, provided that it is possible to identify and select for beneficial alleles of relevant major genes. Since the advent of genome mapping, it has become possible to identify genes affecting quantitative traits (quantitative trait loci, QTL) by looking for associations between the trait and molecular markers distributed evenly across the genome of animals for which maps are available. Importantly, for selection purposes, the heritability of such marker phenotypes is 1.0.

The Chinese Meishan breed of pig is known to produce about 4 extra piglets per litter than the most prolific European breeds. Genes for prolificacy (litter size) from this breed would be of great value in programmes aimed at increasing the litter size of commercial Western pig breeds. Indeed a genetic marker associated with the oestrogen receptor gene (ESR) of the Meishan has been shown to have beneficial effects on litter size and is described in WO92/18651.

The Booroola Merino breed of sheep is extremely prolific. Litter sizes of three or more are common. The significantly increased prolificacy of this breed has been shown to be due to the action of a single gene, FECB (for review see G W Montgomery, et al, *Endocrine Reviews*, 13: 309–328 (1992)). Genetic mapping using human DNA markers has shown that the human version of FECB is located on chromosome 4 (G W Montgomery, et al, *Nature Genetics*, 4: 410–114 (1993)) and is closely associated with the gene encoding secreted phosphoprotein-1 (SPP-1), also known as osteopontin (OPN), 2ar, bone sialoprotein-1, 44 kDa bone phosphoprotein and tumour secreted phosphoprotein. Comparative mapping (H Ellegren, et al, *Genomics*, 17: 599–603 (1993) has shown that human chromosome 4 and porcine chromosome 8 are highly similar (syntenic). The porcine SPP-1 gene is also located on chromosome 8.

More recently, it has been shown that a FECB-linked marker in cattle does not act as a marker for increased litter size in herds selected for increased ovulation rate (Blattman et al, *Mid-West Animal Science Meeting*, 18: 43 (1995)).

However, we have surprisingly found that, in pigs, certain DNA markers for OPN are associated with litter size, and thus can be used to select for pigs with a greater chance of producing increased litter size and to select against pigs which have alleles indicating smaller litter sizes. As used herein "increased litter size" means a significant increase in litter size above the mean of a given population.

It is interesting to note that there is an apparent break point in the chromosome synteny around OPN between sheep, cattle and man on the one hand and mouse and pig on the other (Montgomery et al, *J. Reproduction and Fertility supplement*, 49:113–121 (1995)). This suggests that the structure of the chromosome may be altered in this region, between animals having large litters (mouse and pig) and those with small litters (man, sheep and cow), such that the effect of the major gene for fecundity is modified. Possible explanations include the expression of the major gene may have been increased or decreased by being brought into a more transcriptionally active or inactive region; the major gene may have been brought directly under the control of an altered promoter element; the position of the major gene relative to OPN may have been changed such that OPN becomes a more useable marker in assessing litter size potential in the pig than in sheep or cattle.

Thus, in a first aspect, the present invention provides a method for screening pigs to determine those more likely to produce larger litters, and/or those less likely to produce larger litters, which method comprises the steps:
 (i) obtaining a sample of genomic DNA from a pig; and
 (ii) analysing the genomic DNA obtained in (i) to determine which OPN allele(s) is/are present.

Suitably, step (ii), namely the determination of OPN alleles, is carried out by looking for particular DNA markers linked either directly or indirectly to OPN.

Association between genetic markers and genes responsible for a particular trait can be disrupted by genetic recombination. Thus, the closer the physical distance between the marker and the gene in question, the less likely it is that recombination will separate them. It is also possible to establish linkage between specific alleles of alternative DNA markers and alleles of DNA markers known to be associated with a particular gene (e.g. the OPN gene discussed herein), which have previously been shown to be associated with a particular trait. Thus, in the present situation, taking the OPN gene, it would be possible, at least in the short term, to select for pigs likely to produce larger litters, or alternatively against pigs likely to produce smaller litters, indirectly, by selecting for certain alleles of an OPN associated marker through the selection of specific alleles of alternative chromosome 8 markers. Examples of such markers known to be linked to OPN on porcine chromosome 8 include Sw61, Sw1085, Sw194, Sw16, SW790 and SO178, which markers are all microsatellites.

In a further embodiment of the invention a number of such markers are used. For example, pairs of markers might be utilised to bracket the major gene to reduce any possible effects of recombination. Examples of such combinations of markers include SO178 and SW61 and SO178 and SW790.

Since the effect may be related to the difference in gene orders of pigs (and mice) and sheep (and humans and cattle), this suggests that the most useful second marker will be in the non-homologous (non-syntenic) region of pig chromosome 8. An example of a suitable combination of markers known to bracket this region would be OPN and SO178. However, the skilled man will appreciate that other useful markers could routinely be identified.

A particular genetic marker associated with OPN is a microsatellite. These are simple sequence repeats of 4, 3 or, more usually, 2 nucleotides, which occur essentially at random around the genome at approximately every 50,000 bases (about 60,000 microsatellites per haploid genome). Stuttering of DNA polymerase during replication and unequal crossing-over during recombination are thought to result in the loss or gain of repeat units. This means that microsatellites are usually polymorphic and can have several repeat length alleles.

An example of a microsatellite associated with a given gene is $(CA)_n$, resulting in possible repeat unit length alleles, e.g. $(CA)_2$, $(CA)_9$, $(CA)_{10}$, $(CA)_{11}$ and $(CA)_{12}$.

Using primers capable of hybridising (for example, under stringent conditions) to regions flanking the microsatellite associated with the given gene, in combination with standard PCR techniques, PCR products of differing lengths can be generated, the length being dependent on the particular repeat unit length allele of the microsatellite.

Analysing the association of such PCR products using the microsatellite associated with the OPN gene with litter size has allowed marker length alleles associated with increased, and decreased, litter size to be determined in pigs.

Suitable primer pairs which will hybridise to flanking regions of such microsatellites include those having the following sequence:
GCTAGTTAATGACATTGTACATAA; or (SEQ ID NO 1)
CCAATCCTATTCACGAAAAAGC; and (SEQ ID NO 2)
GTGTCATGAGGTTTTTTCCACTGC; or (SEQ ID NO 3)
CAACCCACTTGCTCCCAC (SEQ ID NO 4).

In particular, repeat unit length alleles for the above-noted microsatellite marker, designated 132 and 136, have been found to be associated with increased litter size in pigs. In addition, the repeat unit length allele, designated 112, has been found to be associated with reduced litter size in pigs.

In fact, the allele associated with increased litter size predominantly derived from a European parent stock. This is contrary to expectations since, as discussed above, the Meishan has four extra piglets per litter than either Landrace or Duroc, and it might have been expected that beneficial markers would have been associated with genes inherited from the Meishan parent stock.

In a second aspect the present invention provides a method of screening pigs to determine those more likely to produce larger litters, and/or those less likely to produce larger litters, which method comprises the steps:
(i) obtaining a sample of genomic DNA from a pig;
(ii) hybridising the genomic DNA from (i) with one or more suitable primers;
(iii) carrying out one or more PCR cycles using the hybridised nucleic acid from (ii); and
(iv) analysing the length of the PCR product obtained in (iii).

Suitably, the methods of the present invention are carried out using reagents and instructions presented in the form of a kit.

Thus, in a third aspect, the present invention provides a kit for screening pigs to determine those more likely to produce larger litters, and/or those less likely to produce larger litters, which comprises one or more reagents or materials capable of identifying OPN alleles in a sample of pig genomic DNA.

A preferred kit of the invention will comprise reagents or materials capable of identifying alleles associated with DNA markers linked to the OPN gene, eg the microsatellite marker. Such a kit -would most preferably comprise one or more DNA primers optionally together with standard PCR reagents.

Finally, the skilled person will realise that the methods and kits described herein can be used in conjunction with other already described methods and kits to screen pigs to determine those more likely to produce larger litters (or those less likely to). An example of such other methods and kits are those described in WO92/18651. It would, of course, be possible to produce combined kits which could be used to screen pig DNA using both methods.

In WO-A-9218651 and U.S. Ser. No. 08/312312 there are disclosed methods for determining which pigs are more likely to produce larger litter sizes based on a linkage with the ESR gene. The skilled man will appreciate, therefore, that the screening methods of the present invention can be combined with the earlier disclosed ESR screening methods to provide a yet more powerful tool for such determinations. Thus, in a further aspect, the present invention provides a method for screening pigs to determine those more likely to produce larger litters, and/or those less likely to produce larger litters, which method comprises the steps:
(i) obtaining a sample of genomic DNA from a pig;
(ii) analysing the genomic DNA obtained in step (i) to determine which OPN allele(s) is/are present; and
(iii) analysing the genomic DNA obtained in step (i) to determine which alele(s) of at least one other gene linked to litter size in pigs is/are present.

In one preferred embodiment of this aspect of the invention the at least one other gene is the ESR gene, as described in WO-A-9218651 and U.S. Ser. No. 08/312312.

In a final aspect the present invention provides a kit for screening pigs to dtermine those more likely to produce larger litters, and/or those less likely to produce larger litters, which comprises one or more reagents or materials capable of identifying OPN alleles in a sample of pig genomic DNA, together with one or more reagents or materials capable of identifying alleles of at least one other gene linked to litter size in pigs in a sample of pig genomic DNA.

Preferred features of each aspect of the invention are applicable to each other aspect mutatis mutandis.

The invention will now be described with reference to the following examples, which should in no way be construed as limiting the invention.

EXAMPLE 1

DNA Preparation

DNA can be prepared from any source of tissue containing cell nuclei, for example white blood cells, hair follicles, ear notches and muscle. The procedure outlined here relates to blood cell preparations; other tissues can be processed similarly by directly suspending material in K buffer and then proceeding from the same stage of the blood procedure. The method outlined here produces a cell lysate containing crude DNA which is suitable for PCR amplification. However, any method for preparing purified or crude DNA should be equally effective.

Blood should be collected in 50 mM EDTA pH 8.0 to prevent coagulation. 50 µl of blood was dispensed into a small microcentrifuge tube (0.5 ml Eppendorf or equivalent) 450 µl of TE buffer was added to lyse the red blood cells (haem groups inhibit PCR) and the mix vortexed for 2 seconds. The intact white and residual red blood cells were then centrifuged for 12 seconds at 13,000 g in a microcentrifuge. The supernatant was removed by gentle aspiration using a low pressure vacuum pump system. A further 450 µl of TE buffer was then added to lyse the remaining red blood cells and the white blood cells collected by centrifugation as before. If any redness remained in the pellet, this process was repeated until the pellet was white. After removal of the last drop of supernatant from the pelleted white blood cells, 100 μl of K buffer containing proteinase K was added and the mixture incubated at 55° C. for 2 hours. The mixture was then heated to 95–100° C. for 8 minutes and the DNA lysates stored at −20° C. until needed.

Reagents

TE buffer:
  10 mM TRIS-HCl pH 8.0
  1mM EDTA

K buffer:
  50 mM KCl
  10mM TRIS-HCl pH 8.3
  2.5mM $MgCl_2$
  0.5% Tween 20

Prior to use for lysates 10 μl of 20 mg/ml proteinase K (Boehringer Mannheim) per 1.0 ml of K buffer was added.

PCR

Reactions were set up as follows in thin walled 0.25 ml tubes (Perkin Elmer):
  1.5 μl 10× buffer;
  1.5 μl 15 mM MgCl;
  1.5 μl 2 mM dNTPs (Pharmacia);
  0.5 μl of each primer at 5 mM (Genosys);
  9 μl sterile deionised water;
  0.1 μl (0.5 units) AmpliTaq DNA polymerase (Perkin Elmer);
  1 μl DNA lysate.

Reaction tubes were then placed on a Perkin Elmer 9600 thermal cycler and PCR carried out according to the regime indicated below:
  94° C. for 4 minutes;
  30 cycles of 94° C. for 30 seconds, 58° C. for 1 minute; and 72° C. for 1 minute;
  72° C. for 4 minutes;
  4° C. until required.

Reagents

| | | |
|---|---|---|
| 10x PCR buffer | 100 Mm Tris-HCl pH 8.3 (25° C.), 500 mM KCl | |
| Forward primer | GCTAGTTAATGACATTGTACATAA | (SEQ ID NO 1) |
| or | CCAATCCTATTCACGAAAAAGC | (SEQ ID NO 2) |
| Reverse primer | GTGTCATGAGGTTTGTGCCACTGC | (SEQ ID NO 5) |
| or | CAACCCACTTGCTCCCAC | (SEQ ID NO 4) |

If one of the primers is labelled with a fluorescent marker, the resulting products can be analysed on an automated DNA sequencer such as the Applied Biosystems 373 DNA Sequencer using Genescan and Genotyper software.

EXAMPLE 2

Polyacrylamide Gel Electrophoresis

5 μl of the PCR products were mixed with 2 μl of loading buffer and separated on a non-denaturing polyacrylamide slab gel in 1×TBE buffer at 100V for 4 hours. The gel was then stained in a 50 ng/ml solution of ethidium bromide for 30 minutes and the PCR products visualised and photographed on a UV light transilluminator. PCR product sizes in base pairs were then estimated from relative mobilities as compared with known molecular weight markers run on the same gel. The size estimate of PCR products reflects the length of the microsatellite allele.

PCR products were also analysed on an Applied Biosystems DNA Sequencer following the use of a fluorescently labelled primer in the PCR.

Results

OPN Allele Frequencies

Results for OPN allele frequencies in different pig populations are presented in Table 1.

TABLE 1

OPN Allele Frequencies in Different Pig Populations

| Population | OPN Allele | Number | Percentage |
|---|---|---|---|
| Landrace | 112 | 3 | 21 |
| | 132 | 6 | 43 |
| | 136 | 2 | 14 |
| | 142 | 3 | 21 |
| Meishan | 132 | 2 | 17 |
| | 140 | 8 | 67 |
| | 142 | 1 | 8 |
| | 154 | 1 | 8 |
| L93 | 112 | 10 | 3 |
| | 122 | 2 | 1 |
| | 124 | 30 | 8 |
| | 132 | 39 | 10 |
| | 134 | 1 | 0 |
| | 136 | 36 | 9 |
| | 140 | 171 | 43 |
| | 142 | 60 | 15 |
| | 153 | 2 | 1 |
| | 154 | 43 | 11 |
| L94 | 124 | 45 | 28 |
| | 132 | 15 | 9 |
| | 136 | 9 | 6 |
| | 140 | 84 | 52 |
| | 154 | 9 | 6 |

L93 Animals from a population founded by a Landrace × Meishan cross.
L94 Animals from a population founded by Duroc × Meishan cross.

Statistical Analysis

Female animals derived from L93 and L94 were scored for litter size (both total number born (TNB) and number born alive (NBA)), over several parities if possible, and these data were compared with OPN microsatellite genotypes for the same animal set. Statistical associations between litter size and OPN genotypes were investigated using the method of least squares to fit a general linear model. Least Squares Means (LSMs) for litter size were estimated for each OPN genotype. LSMs are the means adjusted for other effects in the model which could affect litter size.

The effect of individual OPN alleles was further dissected using an allele substitution model in which animals were classified into groups depending on whether they carried 0, 1 or 2 copies of a particular allele. LSMs for litter size were estimated for each group. The results for L93 are shown in Table 2.

TABLE 2

Allele Substitution Data for L93.

| | | Number of Copies of Alleles | | | | | | | |
|---|---|---|---|---|---|---|---|---|---|
| | | 0 | | 1 | | 2 | | | |
| Allele | Trait | LSM | n | LSM | n | LSM | n | Model | OPN |
| 112 | TNB | 13.0 | 306 | 11.8 | 21 | | 0 | + | + |
| | NBA | 11.8 | | 10.9 | | | | NS | NS |
| 124 | TNB | 12.9 | 281 | 13.0 | 46 | | 0 | + | NS |
| | NBA | 11.8 | | 11.6 | | | | NS | NS |

TABLE 2-continued

Allele Substitution Data for L93.

| | | Number of Copies of Alleles | | | | | | | |
|---|---|---|---|---|---|---|---|---|---|
| | | 0 | | 1 | | 2 | | | |
| Allele | Trait | LSM | n | LSM | n | LSM | n | Model | OPN |
| 132 | TNB | 12.8 | 260 | 13.3 | 57 | 14.3 | 10 | + | NS |
|  | NBA | 11.5 |  | 12.3 |  | 13.9 |  | NS | * |
| 136 | TNB | 12.9 | 271 | 12.9 | 53 | 17.5 | 3 | * | + |
|  | NBA | 11.8 |  | 11.6 |  | 11.1 |  | NS | NS |
| 140 | TNB | 12.7 | 81 | 13.1 | 175 | 12.8 | 71 | + | NS |
|  | NBA | 11.5 |  | 11.9 |  | 11.6 |  | NS | NS |
| 142 | TNB | 13.0 | 253 | 12.8 | 68 | 11.3 | 6 | + | NS |
|  | NBA | 11.8 |  | 11.7 |  | 9.8 |  | NS | NS |
| 153 | TNB | 12.9 | 320 | 13.0 | 7 |  | 0 | + | NS |
|  | NBA | 11.8 |  | 10.9 |  |  |  | NS | NS |
| 154 | TNB | 13.0 | 284 | 12.5 | 39 | 11.5 | 4 | + | NS |
|  | NBA | 11.8 |  | 11.4 |  | 10.7 |  | NS | NS |

Significance level: *, P < 0.05; +, P < 0.10; NS, P > 0.10.
Model includes season, AI or natural service, parity, generation and OPN genotype.
TNB total number born
NBA number born alive
LSM least squares means
n number of records, i.e. litters It can be seen from the data that allele 112 appears to be related to a negative effect on litter size, whereas positive trends are seen for alleles 132 (NBA) and 136 (TNB). The data presented in Table 1 suggests that while alleles 112 and 136 were probably derived from the Landrace, allele 132 could have been derived from either the Landrace or Meishan ancestry. However, as the 132 allele is more than twice as common in the Landrace as the Meishan, it is likely that a significant proportion of the 132 alleles in L93 derive from the Landrace.

In order to investigate the potential of these alleles to act as predictors of litter size, additional data from L94 were included in the analysis. Allele 112 was not found in this line (presumably this allele is not found in Duroc). The combined data for alleles 132 and 136 are shown in Table 3.

TABLE 3

| | | Number of Copies of Alleles | | | | | | | |
|---|---|---|---|---|---|---|---|---|---|
| | | 0 | | 1 | | 2 | | Significance of | |
| Allele | Trait | LSM | n | LSM | n | LSM | n | Model | OPN |
| 132 | TNB | 12.2 | 375 | 12.9 | 82 | 14.2 | 12 | *** | + |
|  | NBA | 10.9 |  | 11.9 |  | 13.5 |  | ** | ** |
| 136 | TNB | 12.3 | 393 | 12.3 | 73 | 16.9 | 3 | *** | + |
|  | NBA | 11.1 |  | 11.0 |  | 10.5 |  | NS | NS |

Significance levels: *, P < 0.001; , P < 0.01; +, P < 0.05; NS, not significant.

These data show that only allele 132 had a significant positive effect for litter size for both TNB and NBA. Although allele 136 was close to significance for TNB, it is probable that the effect here is due to a small amount of 136/136 animals (3) with very high observations.

The association between OPN allele 132 and high litter size has now been demonstrated in two different lines of pig (L93 and L94). This indicates that a QTL affecting litter size is closely associated with the porcine OPN gene. However, it is possible that in other families, lines or breeds of pig that a different OPN allele will be associated with increased litter size.

The results of a re-analysis of the data for L93 and L94 and for an additional line L07 (a large white line) is shown below in table 4 using an alternative model. This involved fitting each OPN allele as a variable and coding each animal with a 0, 1 or 2 for each allele (ie 0, 1 or 2 copies of each allele).

Fixed effects were herd-season-service type and parity. Sire was included as a random effect. ESR and OPN were fitted as covariables. All data per line were included, not just full- or half-sib families. OPN alleles with less than 10 litters of a second genotype were excluded from the analyses.

Traits analysed were total number born (TNB) and number born alive (NBA).

Three models were run for each line including the fixed, random and ESR effects as given above.
1. Model excluding OPN
2. Model including all OPN alleles
3. Model including OPN alleles individually −2logliklihood was obtained for each model. Significance of the model was calculated by subtracting the log liklihood from models 2 or 3 from model 1 and comparing the result against a Chi-squared distribution. Degrees of freedom (df) used was the difference between the two models.

The levels of significance per line for model 2 and any significant alleles in model 3 are given in the table below.

TABLE 4

| | | TNB | | NBA | |
|---|---|---|---|---|---|
| Line | Model/ allele | Significance | Allele substitution effect | Significance | Allele substitution effect |
| 7 | 2 | P < 0.10 |  | P < 0.10 |  |
|  | 3/OPN122 | P < 0.05 | −1.30 | P < 0.05 | −1.37 |
| 93 | 2 | P < 0.10 |  | P < 0.05 |  |
|  | 3/OPN112 | P < 0.10 | −0.87 | P < 0.10 | −0.92 |
|  | 3/OPN132 | NS | +0.49 | P < 0.05 | +0.72 |
|  | 3/OPN154 | P < 0.10 | −0.72 | NS | −0.46 |
| 94 | 2 | P < 0.01 |  | P < 0.05 |  |
|  | 3/OPN124 | P < 0.10 | −0.83 | P < 0.10 | −0.74 |
|  | 3/OPN132 | P < 0.01 | +1.62 | P < 0.05 | +1.42 |

The following conclusions can be drawn from this data:
1. OPN accounted for a significant amount of variation in litter size (after including ESR) for L07 (P<0.10); L93 (TNB: P<0.10; NBA: P<0.05) and L94 (TNB: P<0.01; NBA: P<0.05).
2. OPN allele 132 showed a significant positive effect on litter size in L93 and L94.
3. Other alleles OPN122 (L07), OPN112 and OPN154 (L93) and OPN124 (L94) showed significant negative effects.

EXAMPLE 3

Genomic DNA samples from a further line L03 (another large white based line) were obtained and analysed. The results are shown below in table 5. 416 animals with 1,010 litter records were analysed.

Several different models were run. All models included the effect of farm-month farrowed, parity and sire. ESR was fitted as a co-variate in all analyses.

Traits analysed were total number born (TNB) and number born alive (NBA).

Models used:
1. Total number born=farrow-month+sire+ESR+OPN allele
2. TNB or NBA=farrow-month+sire+ESR+OPN112+ OPN122 etc

TABLE 5

| Line | Model/Allele | TNB Significance | TNB Allele substitution effect | NBA Significance | NBA Allele substitution effect |
|------|--------------|------------------|--------------------------------|------------------|--------------------------------|
| 03 | 1/OPN124 | P < 0.01 | +0.72 | | |
| | 1/OPN136 | P < 0.15 | −0.27 | | |
| | 1/OPN138 | P < 0.15 | +2.04 | | |
| | 1/OPN142 | P < 0.15 | −0.27 | | |
| | 2/OPN112 | NS | +0.34 | NS | +0.58 |
| | 2/OPN122 | NS | −0.13 | NS | −0.18 |
| | 2/OPN124 | <0.05 | +0.65 | NS | +0.33 |
| | 2/OPN132 | NS | +0.31 | NS | +0.08 |
| | 2/OPN136 | NS | −0.29 | NS | −0.37 |
| | 2/OPN138 | <0.15 | +2.06 | NS | +1.81 |
| | 2/OPN140 | NS | −0.11 | NS | −0.16 |
| | 2/OPN142 | NS | −0.22 | <0.15 | −0.40 |
| | 2/OPN144 | NS | −1.06 | NS | −1.16 |
| | 2/OPN146 | NS | +1.08 | NS | +0.15 |
| | 2/OPN154 | NS | +0.02 | NS | −0.02 |

This data indicates that OPN 124 shows a significant (P<0.01) positive effect for TNB of 0.7 for each copy of the allele. In addition, OPN 142 showed a trend toward a negative effect on litter size in L03, a similar effect to that seen for L93.

As discussed above, another gene ESR, has been shown to affect litter size in pigs and it is likely that other genes linked with litter size will be identified in the future. We investigated whether certain beneficial allele combinations of the two separate genes, OPN and ESR, provide an additive effect on litter size.

To test this possibility we looked at the association between litter size and various combinations of ESR and OPN alleles. The results presented below in tables 4 and 5 show that indeed beneficial alleles of OPN can combine positively with beneficial alleles of ESR, such that an even greater litter size advantage can be realised than can be achieved through using beneficial alleles of OPN or ESR alone.

TABLE 4

Allele substitution effect for OPN and ESR markers on litter size (TNB) in line 93 (L93)

| Marker | Allele substitution effect for TNB | Significance |
|--------|------------------------------------|--------------|
| OPN 132 | +0.49 | ns |
| ESR B | +0.34 | ns |
| OPN 132 or ESR B | +0.39 | P < 0.1 |

TABLE 5

Expected litter size (TNB) advantage for various combinations of CPN and ESR markers in line 93 (L93) based on data presented in Table 4

| Genotype | | | | Litter size effect |
|---|---|---|---|---|
| ESR | ESR | OPN | OPN | (TNB) |
| — | — | — | — | 0.00 |
| B | — | — | — | +0.34 |
| B | B | — | — | +0.68 |
| — | — | 132 | — | +0.49 |
| — | — | 132 | 132 | +0.98 |
| B | — | 132 | — | +0.83 (+0.78) |
| B | B | 132 | — | +1.17 (+1.12) |
| B | — | 132 | 132 | +1.32 (+1.27) |
| B | B | 132 | 132 | +1.66 (+1.56) |

Litter size effects assume complete additivity (OPN 132=+0.49; ESR B=+0.34) exceptthose in brackets which assume the effect of OPN 132 or ESR B=+0.39.

For the purposes of this invention, the following documents are incorporated by reference to the extent that they facilitate making or using the invention:

Rhorer et al., Genetics, 136:231–245 (1994).
Genbank Entry for Locus SSSPP1, Accession No. X16575.
Wrana et al., Nucl. Acids Res., 17:10119 (1989).

What is claimed is:

1. A method for screening pigs to determine those more likely to produce larger litters, and/or those less likely to produce larger litters, which method comprises the steps:
   (i) obtaining a sample of genomic DNA from a pig; and
   (ii) analysing the genomic DNA obtained in (i) to determine which osteopontin (OPN) allele(s) is/are present.

2. A method as claimed in claim 1 wherein the determination of OPN alleles in step (ii) comprises determining the presence of at least one allele associated with at least one DNA marker linked either directly or indirectly to OPN.

3. A method as claimed in claim 2 wherein the DNA marker is a microsatellite.

4. A method as claimed in claim 3 wherein the DNA marker is Sw1085, Sw194, Sw16, Sw790, So178 or Sw61.

5. A method as claimed in claim 4 wherein one or more primers capable of hybridising to a region associated with the microsatellite are added to the sample of genomic DNA followed by one or more cycles of PCR to generate primer extension products.

6. A method as claimed in claim 5 wherein the OPN allele or alleles present in the sample of genomic DNA is determined by reference to the length of the primer extension product(s).

7. A method as claimed in claim 5 or claim 6 wherein one or more of the following primers are employed:
   GCTAGTTAATGACATTGTACATAA; (SEQ ID No 1)
   CCAATCCTATTCACGAAAAAGC; (SEQ ID No 2)
   GTGTCATGAGGTTTTTTCCACTGC; or (SEQ ID No 3)
   CAACCCACTTGCTCCCAC. (SEQ ID No 4).

8. A method of screening pigs to determine those more likely to produce larger litters, and/or those less likely to produce larger litters, which method comprises the steps:

(i) obtaining a sample of genomic DNA from a pig;

(ii) hybridising the genomic DNA from (i) with one or more suitable primers;

(iii) carrying out one or more PCR cycles using the hybridised nucleic acid from (ii); and (iv) analysing the length of the PCR product obtained in (iii), wherein PCR according to step (iii) in the presence of said primers produces PCR products corresponding to at least one allele associated with at least one DNA marker linked either directly or indirectly to OPN.

9. A method as claimed in claim 8 wherein one or more of the following primers are employed:

GCTAGTTAATGACATTGTACATAA; (SEQ ID No 1)
CCAATCCTATTCACGAAAAAGC; (SEQ ID No 2)
GTGTCATGAGGTTTTTTCCACTGC; or (SEQ ID No 3)
CAACCCACTTGCTCCCAC. (SEQ ID No 4).

10. A method of determining which allele or alleles for a DNA marker associated with the pig OPN gene is/are associated with larger litter size, which comprises the steps of:

(i) obtaining genomic DNA from one or more pigs;

(ii) determining which allele or alleles are present for a particular DNA marker associated with the OPN gene;

(iii) comparing the result of step (ii) with a similar determination carried out for one or more pigs known to produce larger litter sizes.

11. A method for screening pigs to determine those more likely to produce larger litters, and/or those less likely to produce larger litters, which method comprises the steps:

(ii) obtaining a sample of genomic DNA from a pig;

(ii) analysing the genomic DNA obtained in step (i) to determine which OPN allele(s) is/are present; and (iii) analysing the genomic DNA obtained in step (i) to determine which allele(s) of at least one other gene linked to litter size in pigs is/are present.

12. A method as claimed in claim 11 wherein the at least one other gene is the oestrogen receptor (ESR) gene.

13. A method as claimed in claim 11 or claim 12, wherein the determination of OPN alleles in step (ii) comprises determining the presence of at least one allele associated with at least one DNA marker linked either directly or indirectly to OPN.

14. A method as claimed in claim 8 wherein the DNA marker is a microsatellite.

15. A method as claimed in claim 14 wherein the DNA marker is Sw1085, Sw194, Sw16, Sw790, So178 or Sw61.

16. A method as claimed in claim 13 wherein the DNA marker is microsatellite.

17. A method as claimed in claim 16 wherein the DNA marker is Sw1085, Sw194, Sw16, Sw790, So178 or Sw61.

18. A method as claimed in claim 17 wherein one or more primers capable of hybridising to a region associated with the microsatellite are added to the sample of genomic DNA followed by one or more cycles of PCR to generate primer extension products.

19. A method as claimed in claim 18 wherein the OPN allele or alleles present in the sample of genomic DNA is determined by reference to the length of the primer extension product(s).

20. A method as claimed in claim 19 wherein one or more of the following primers are employed:
GCTAGTTAATGACATTGTACATAA; (SEQ ID No. 1)
CCAATCCTATTCACGAAAAAGC; (SEQ ID No. 2)
GTGTCATGAGGTTTTTTCCACTGC; or (SEQ ID No. 3)
CAACCCACTTGCTCCCAC. (SEQ ID No. 4).

21. A method as claimed in claim 20 wherein one or more of the following primers are employed:
GCTAGTTAATGACATTGTACATAA; (SEQ ID No. 1)
CCAATCCTATTCACGAAAAAGC; (SEQ ID No. 2)
GTGTCATGAGGTTTTTTCCACTGC; OR (SEQ ID No. 3)
CAACCCACTTGCTCCCAC. (SEQ ID No. 4).

* * * * *